United States Patent [19]

Ko et al.

[11] Patent Number: 5,738,923
[45] Date of Patent: Apr. 14, 1998

[54] MEDICAL TUBING AND ASSEMBLIES

[75] Inventors: John H. Ko, Woodbury; Lester B. Odegaard, Afton; James R. Boardman, White Bear Lake, all of Minn.

[73] Assignee: Minnesota Mining and Manufacturing Company, St. Paul, Minn.

[21] Appl. No.: 442,398

[22] Filed: May 16, 1995

[51] Int. Cl.$^6$ ............................................. A61M 25/00
[52] U.S. Cl. .................... 428/36.91; 138/118; 138/137; 138/177; 428/36.92; 428/36.9; 428/500; 428/516; 428/515
[58] Field of Search .................... 138/118, 137, 138/177, DIG. 7; 525/195, 196, 221; 428/36.8, 36.9, 36.91, 36.92, 500, 515, 516

[56] References Cited

U.S. PATENT DOCUMENTS

| | | | |
|---|---|---|---|
| 3,287,315 | 11/1966 | Connor et al. | 138/137 |
| 3,384,089 | 5/1968 | Shriner | 138/137 |
| 3,429,954 | 2/1969 | Atkins et al. | 138/137 |
| 3,561,493 | 2/1971 | Maillard | 138/141 |
| 3,584,656 | 6/1971 | Van Assendelft | 138/137 |
| 3,819,792 | 6/1974 | Ono et al. | 264/95 |

(List continued on next page.)

FOREIGN PATENT DOCUMENTS

| | | |
|---|---|---|
| 0 217 585 | 4/1987 | European Pat. Off. . |
| 0 380 270 | 1/1990 | European Pat. Off. . |
| 0 448 886 | 2/1991 | European Pat. Off. . |
| 0 422 632 | 4/1991 | European Pat. Off. . |
| 0 477 025 A2 | 3/1992 | European Pat. Off. ........ B32B 27/08 |
| 0 588 667 | 3/1994 | European Pat. Off. . |
| 28 43 061 | 4/1980 | Germany . |
| 2 210 047 | 6/1989 | United Kingdom . |
| WO 93/23093 | 11/1993 | WIPO . |
| WO 94/08769 | 4/1994 | WIPO . |
| WO 95/04652 | 2/1995 | WIPO . |

OTHER PUBLICATIONS

*Encyclopedia of Polymer Science and Engineering*, vol. 17, pp. 50–51, John Wiley & Sons, 1989.
"Proposed Dioxins Control Measure for Medical Waste Incinerators," Staff Report—State of California Air Resources Board Stationary Source Division, May 25, 1990.
Taravella, S., "Hospitals Dispose of Destructive Waste Habits," Modern Healthcare, pp. 26–30, Dec. 24/31, 1990.
Vogg, H., et al., "Contribution to Solving the Problem of Dioxins Generated during Waste Incineration," Chem. Eng. Technol. 13 (1990) PP. 221–229.
Paprock, J., The MHA Recycling & Conservation Guide, Minnesota Hospital Association, 1991.
Ellis, J.R., "Plasticizers—Under Scrutiny Again," Medical Device & Diagnostic Industry, vol. 13, No. 3, pp. 88–89, Mar. 1991.
Menagh, M., The Business of Going Green, OMNI, vol. 13, No. 9, pp. 42–48, Jun. 1991.
Erickson, D., "Can plastics be burned safely?," Plastics World, Sep. 1989.
"Dioxin and Other Pollutants from Incineration of Medical Waste," Perspectives on Medical Waste, A Report of The Nelson A. Rockefeller Institute of Government, State University of New York, Sponsored by the Medical Waste Policy Committee, Jun. 1989, pp. II.20–II–24.
"Standard Test Method for Flow Rates of Thermoplastics by Extrusion Plastometer[1]", ASTM Designation: D 1238–90b, pp. 272–280.
Encyclopedia of Polymer Science and Engineering, vol. 8, pp. 393–423, John Wiley & Sons, 1987.
"EXCEL" product literature, pp. 18–19.
McGaw, Inc., Intravenous products literature, pp. 10–13.

*Primary Examiner*—Charles Nold
*Attorney, Agent, or Firm*—Kinney & Lange, P.A.

[57] ABSTRACT

Tubing and tubing assemblies are provided that are made from a blend of an ionic and a non-ionic polymer. The tubing may be made by blending and extruding the polymers. The assemblies may be made by bonding the tubing to a plastic fluid transporting component such as a cassette or bag.

17 Claims, 2 Drawing Sheets

U.S. PATENT DOCUMENTS

| | | | |
|---|---|---|---|
| 4,044,799 | 8/1977 | Higbee et al. | 138/137 |
| 4,190,088 | 2/1980 | Lalikos et al. | 138/137 |
| 4,211,741 | 7/1980 | Ostoich | 138/137 |
| 4,222,379 | 9/1980 | Smith | 128/214 D |
| 4,272,559 | 6/1981 | Asai et al. | 427/54.1 |
| 4,298,714 | 11/1981 | Levin et al. | 525/330 |
| 4,305,983 | 12/1981 | Hoppe et al. | 428/36 |
| 4,539,263 | 9/1985 | Hoh | 428/500 |
| 4,550,141 | 10/1985 | Hoh | 525/221 |
| 4,574,173 | 3/1986 | Bennett | 219/10.53 |
| 4,578,413 | 3/1986 | Sterling | 524/269 |
| 4,616,064 | 10/1986 | Zukosky et al. | 525/92 |
| 4,627,844 | 12/1986 | Schmitt | 604/264 |
| 4,643,926 | 2/1987 | Mueller | 138/137 |
| 4,685,090 | 8/1987 | Krevor | 138/137 |
| 4,707,389 | 11/1987 | Ward | 428/36 |
| 4,766,174 | 8/1988 | Statz | 525/196 |
| 4,803,102 | 2/1989 | Raniere et al. | 428/35.2 |
| 4,910,085 | 3/1990 | Raniere et al. | 428/412 |
| 4,948,643 | 8/1990 | Mueller | 138/137 |
| 5,059,375 | 10/1991 | Lindsay | 264/167 |
| 5,064,903 | 11/1991 | Peiffer | 525/196 |
| 5,085,649 | 2/1992 | Flynn | 604/282 |
| 5,091,206 | 2/1992 | Wang et al. | 427/2 |
| 5,116,652 | 5/1992 | Alzner et al. | 428/36.9 |
| 5,158,836 | 10/1992 | Schirmer et al. | 428/336 |
| 5,198,301 | 3/1993 | Hager et al. | 428/355 |
| 5,202,381 | 4/1993 | Parker | 525/85 |
| 5,252,667 | 10/1993 | Parker | 525/85 |
| 5,274,035 | 12/1993 | Chundury | 525/92 |
| 5,284,489 | 2/1994 | Liu et al. | 606/228 |
| 5,294,672 | 3/1994 | Peiffer | 525/196 |
| 5,356,709 | 10/1994 | Woo et al. | 428/376 |
| 5,399,401 | 3/1995 | Powell | 428/36.9 |
| 5,496,291 | 3/1996 | Spencer | 604/280 |

MEDICAL TUBING AND ASSEMBLIES

FIELD

This invention relates to tubing and tubing assemblies, such as medical pumping cassettes, which are suitable to replace conventional polyvinyl chloride (PVC) tubes and assemblies, but without the environmental and health hazards associated with PVC materials. This invention also relates to polymer blends suitable for medical tubing and sheeting.

BACKGROUND

Polyvinyl chloride (PVC) based tubing and tubing assemblies are used in numerous medical products. However, PVC is viewed as hazardous to both the environment and to personal health. Incineration of PVC results in the release of hydrochloric acid (HCl), and PVC is viewed as a major contributor to HCl in incinerator flue gases. Also, PVC is suspected of contributing to polychlorinated dibenzodioxin and furan toxins formed during incineration. Levels of these toxins are up to three times greater in medical infectious waste as compared to municipal waste streams. In addition to incineration concerns, exposure to di-2-ethylhexyl phthalate (DEHP), a common plasticizer used with PVC, may present a number of health related concerns, including reduced blood platelet efficacy and potential links to liver cancer. PVC is also known to adsorb certain drugs, such as nitroglycerin and insulin. This can reduce the efficiency and accuracy of drug delivery.

Despite these concerns, PVC-based tubing and tubing assemblies, continue to be the material of choice in scientific and medical applications. See, e.g., *Encyclopedia of Polymer Science and Technology*, Vol. 17, pg. 50 (1989). The continued use of PVC materials is due, at least in part, to PVC's attractive qualities, including flexibility; toughness; resistance to UV light, gamma irradiation, solvents, cuts, scratches, and acids; clarity or opaqueness as required; and low cost. In addition, PVC's characteristics can be modified through the addition of various additives, such as plasticizers, colorants, and the like. For example, U.S. Pat. No. 4,298,714 discloses a modified PVC material with reduced hydrophilicity due to the addition of various thiol-group compounds to the PVC backbone.

Thermoplastic polymers other than PVC have been used to form single-layer tubing and tubing assemblies. For example, low-density polyethylene, high density polyethylene, polypropylene, ethylene vinyl acetate, and polybutylene have all been used to form single-layer tubing and tubing assemblies. See, e.g., *Encyclopedia of Polymer Science and Technology*, pp. 50–51. Several commercial offerings of non-PVC medical tubing sets are available on the market. For example, B. Braun Melsungen AG from Germany has a non-PVC tubing made of polybutadiene-based material. The Braun tubing is translucent and kinks easily. Baxter International sells tubing of a 3-layer type construction, with the outer layer consisting of plasticized PVC. McCaw, Inc. (Irvine, Calif.) has an intravenous (IV) set tubing which is a two layered tubing. The outer layer is an EVA copolymer and the inner layer is made of polyethylene. However, none of these polymer materials has been successfully used to provide tubing and tubing assemblies with the advantageous characteristics needed to serve as an environmentally compatible replacement for PVC-based materials. In addition, some of the above noted materials are polyolefins or their copolymers. Polyolefins generally have low surface energies which makes them difficult to bond with conventional adhesives or solvents. This is a disadvantage when the making of tubing assemblies is contemplated.

Copending and coassigned U.S. patent application Ser. No. 08/104,256 discusses certain multilayered tubing which mimics most of the properties of comparable PVC tubing, especially with respect to resisting kinking during bending and rekinking in a location that has already been kinked. However, the somewhat complicated multilayer extrusion process tends to raise the price of providing this tubing above that of PVC. This is highly undesirable in the price sensitive disposable medical tubing market.

To date, no tubing nor tubing assemblies exist which provide all the advantageous characteristics of PVC materials, and yet are environmentally compatible upon disposal.

Therefore, there is a need for tubing and tubing assemblies that can be utilized in a wide range of both medical and non-medical products, and that can serve as replacements for PVC-based materials. There is a need for elements of medical devices such as IV infusion therapy sets which are environmentally compatible, and yet capable of satisfying the challenging requirements. Specifically, there is a need for PVC replacement IV and irrigation sets which are preferably free of plasticizer, extremely flexible, yet tough enough to endure their intended use. They preferably are visually transparent, as well as solvent, UV light, and gamma sterilization resistant, and capable of being made for a relatively low cost.

RELATED APPLICATIONS

Of related interest are the following U.S. Patent Applications, cop ending and coassigned U.S. patent application Ser. No. 08/104,256 "MULTILAYERED TUBING" to Wilfong et at; and copending and coassigned U.S. patent application Ser. No. 08/103,082 "MEDICAL DEVICE ASSEMBLIES CONSTRUCTED FROM MULTILAYERED FILMS" to Fanselow et al, both of which are hereby incorporated by reference.

SUMMARY

The present invention solves the above discussed problems by providing a polymer blend which is environmentally compatible, while still being surprisingly tough considering its high flexibility and kink resistance. Tubes and sheets made from this blend have good transparency, are solvent, UV light, and gamma irradiation resistant, and can be made for an acceptable cost.

In a first aspect, the invention provides a tube comprising a polymeric material having at least one lumen therein. The polymeric material is a blend of a thermoplastic ionomer, which particularly imparts the properties of strength and a good surface finish to the blend, and a non-ionic thermoplastic polymer, which particularly imparts the properties of flexibility and kink/rekink resistance to the blend. The tube preferably has a Young's modulus between about 14 to 35 MPa. The invention also provides a method of making this kink resistant tubing; and an entire tubing assembly which includes the novel tubing.

In a second aspect, the invention provides a sheet comprising a blend of a thermoplastic ionomer, which particularly imparts the properties of strength and a good surface finish to the blend, and a non-ionic thermoplastic polymer, which particularly imparts the properties of flexibility and kink/rekink resistance to the blend. The sheet may be used, for example, in the construction of medical plastic fluid transporting components, such as cassettes used for pumping fluids, and medical bags, such as ostomy bags and blood bags.

BRIEF DESCRIPTION OF THE DRAWINGS

FIG. 3b is a side view of the "Kink-o-meter" of FIG. 3a.

DEFINITIONS

Certain terms and phrases are used to describe the tube and tube assembly. Generally, these terms and phrases have the ordinary definitions understood by those of skill in the art. Several, however, have particular meanings as given below.

The term "Young's modulus" means the amount of force per unit area of material needed to elongate the material a unit distance after the stress has been initiated and before the curve of stress against elongation becomes non-linear. The Young's modulus is measured in megaPascals (MPa).

The term "cassette" means a device generally formed of a number of overlaid plastic sheets. The cassette possesses internal passages and/or chambers and/or bubbles suitable for conducting fluids. The cassette may be a pumping cassette suitable for motoring fluids in connection with an infusion pump.

The term "plastic fluid transporting component" means a component formed at least partially of a polymer and having a lumen for conducting fluid. Non-limiting examples include cassettes, tubing, luer locks, injection sites, bag spikes, filters, check valves, and drip chambers.

The term "polymer," unless the context indicates differently, implies both homopolymers and copolymers. "Copolymers" includes polymers having two or more different monomers.

DETAILED DESCRIPTION

Figure 1:
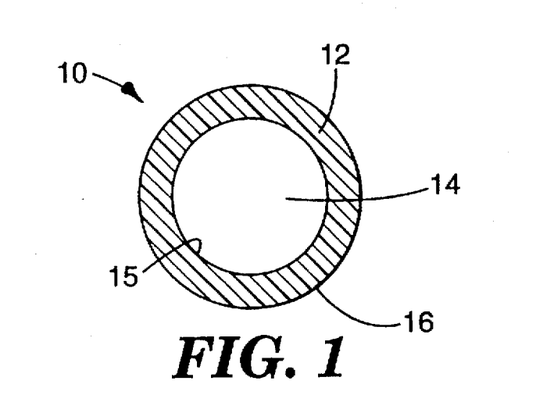
FIG. 1 is a cross-section view through an exemplary tube according to the present invention.

Referring now to FIG. 1, a cross-section view through an exemplary tube 10 according to the present invention is illustrated. The tube 10 is made from a layer 12 of a polymeric material comprising a blend of at least two polymers as defined below, the layer defining a lumen 14, an interior surface 15 and an exterior surface 16.

Figure 2:
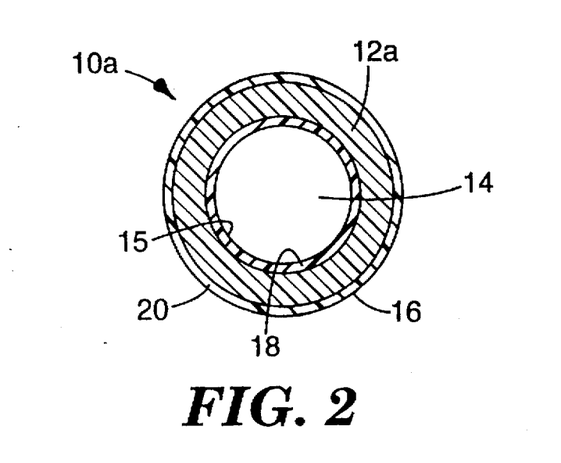
FIG. 2 is a cross-section view through an alternate embodiment of the tube.

Referring now to FIG. 2, a cross-section view through an alternate embodiment of a tube 10a of the present invention is illustrated. Tube 10a has a layer 12a of a blend of at least two polymers, as discussed in connection with FIG. 1, and a separate interior layer 18 and exterior layer 20. Layers 18 and 20 define the lumen 14 and the exterior surface 16 respectively. In this alternate embodiment, interior layer 18 and exterior layer 20 may represent additional polymeric layers coextruded at the same time as layer 12a is extruded, or they may be added in a secondary operation, for example by dipping, spraying or plasma deposition. They may be needed for certain special applications, for example a specialized interior coating may be needed to contain a particular fluid being carded by the tube, or an exterior layer may be needed to bond to a component made of a particular material. In general, the presence of an interior layer 18 and/or an exterior layer 20 are not presently considered preferred due to the expected additional cost. However, multilayered tubes are considered within the broad scope of the invention.

The blend of polymers discussed above in connection with layer 12 (or layer 12a of alternative embodiment 10a) comprises a blend, preferably a homogeneous blend, of at least two polymers. One polymer is a thermoplastic ionomer, preferably present in an amount between about 5 and 90% by weight of the blend, more preferably present in an amount between about 10 and 50% by weight of the blend, and most preferably present in an amount between about 20 and 40% by weight of the blend. The second polymer is a non-ionic thermoplastic polymer preferably present in an amount between about 10 and 95% by weight of the blend, more preferably present in an amount between about 50 and 90% by weight of the blend, and most preferably present in an amount between about 60 and 80% by weight of the blend.

The materials and proportions are such that the tube preferably has a Young's modulus between about 14 and 35 MPa, and more preferably between about 17 and 28 MPa. Such blends are environmentally compatible, yet tough and flexible. Preferably, they are visually transparent, free of plasticizer, solvent, UV light, and gamma irradiation resistant, while offering a relatively low cost.

Preferred blends of the present invention are flexible and may be formed into tubing suitable for medical use. Preferred tubes comprising the polymeric blend exhibit a tensile elongation of at least 300% to break when tested as described in Example 1. More preferred tubes exhibit a tensile elongation of at least 600%, and most preferred tubes exhibit a tensile elongation of at least 750% when tested as described in Example 1.

Preferred blends of the present invention form strong tubing. Preferred tubes comprising the polymeric blend exhibit a tensile strength of at least 12 MPa when tested as described in Example 1. More preferred tubes exhibit a tensile strength of at least 13 MPa, and most preferred tubes exhibit a tensile strength of at least 14 MPa when tested as described in Example 1.

It is common that medical tubing may become exposed to high temperatures, either during shipment or use (e.g., during sterilization). The tubing should preferably not soften during shipment or use as the dimensions or shape of the tube might be affected while in the softened state. An unintended change in size or shape could cause problems. For example, a piece of deformed tubing might not be well adapted to an infusion pump or might kink more easily in the region of the deformation.

The heat stability of a material may be measured using a thermal mechanical analyzer equipped with a 50 mN penetration probe and operated over a temperature sweep from 0° C. to 100° C. at a rate of 10° C. per minute. Preferred blends of the present invention have a softening point above about 60° C., more preferably above about 65° C.

In tubes of the present invention, the thermoplastic ionomer particularly imparts the properties of strength and a good surface finish to the blend. Suitable thermoplastic ionomers includes ionic polymers consisting of an organic backbone and having pendant acidic groups (e.g., carboxylic acid groups, sulfonic acid groups, etc.) which are neutralized either partially or completely with metal or quaternary ammonium ions. In preferred embodiments, the thermoplastic ionomer will be composed of an ionomeric copolymer selected from the group consisting of copolymer of ethylene and acrylic acid-metal cation neutralized salt, or of ethylene and methacrylic acid-metal cation neutralized salt. Two or more different thermoplastic ionomers may be used in the blends of the present invention. Examples of preferred thermoplastic ionomers include ionomeric ethylene-methacrylic acid copolymer with zinc (EMAZ) or sodium (EMAS) neutralization, such as Surlyn™ copolymer manufactured by the E. I. Du Pont de Nemours Co., Wilmington, Del. (Du Pont). Ethylene/acrylate/acrylic acid copolymer with zinc neutralization, such as Iotek™ from Exxon Chemical Co. of Houston, Tex., are also considered suitable.

Best results are obtained when the Young's modulus of the thermoplastic ionomer is between about 14 and 56 MPa, or more preferably between about 17 and 49 MPa. Preferred thermoplastic ionomers have a weight average molecular weights between about 50,000 and 1,000,000 daltons, more preferably between about 70,000 and 500,000 daltons, are most preferably between about 100,000 and 200,000 daltons. Suitable thermoplastic ionomers have a flow rate, when tested according to ASTM D 1238-90b at the temperature used when extruding the blend, preferably between about 0.5 and 20 g/10 min., more preferably between about 0.5 and 10 g/10 min.

In tubes of the present invention, the non-ionic thermoplastic polymer particularly imparts the properties of flexibility and kink/rekink resistance to the blend. The non-ionic thermoplastic polymer is preferably selected from the group consisting of polymers of olefin monomers and copolymers of olefin monomers and substituted olefin monomers. More preferably, the non-ionic thermoplastic polymer within the blend is selected from the group consisting of polymers of a C2 to C4 mono-unsaturated alkene; copolymers of a majority of a C2 to C4 mono-unsaturated alkene with a minority of a substituted olefin monomer such as C4 to C14 mono-unsaturated alkene; or copolymers of a majority of a C2 to C4 mono-unsaturated alkene with a minority of a substituted C2 to C6 mono-unsaturated alkene having a substituent such as carboxylic acid ester groups. Examples of the first class include polyethylene (PE), polypropylene (PP), and copolymers of ethylene with butene (EB) or propylene with butene (PB). Examples of the second class include copolymers of ethylene with octene (EO) or propylene with octene (PO). Examples of the third class include copolymers of olefins such as ethylene or propylene with substituted olefins such as vinyl acetate (EVA or PVA). Other examples of the third class include copolymers of ethylene and n-butyl acrylate, and copolymers of ethylene and ethyl acrylate. Two or more different non-ionic thermoplastic polymers may be used in the blends of the present invention.

Some specific materials which are considered suitable include ethylene/butene copolymer commercially available as Exact™ from Exxon of Houston, Tex.; ethylene/alpha-olefin copolymer commercially available as Tafmer™ from Mitsui Petrochemical Industries of Tokyo, Japan; ethylene/octene copolymer commercially available as Attane™ or Insite™ from Dow Chemical of Midland, Mich.; and ethylene/acetate copolymer commercially available as Elvax™ from Du Pont of Wilmington, Del. or Utrathene™ from Quantum Chemical of New York, N.Y. Best results are obtained when the Young's modulus of the non-ionic thermoplastic polymer is between about 14 and 35 MPa, or more preferably between about 14 and 28 MPa. Preferred non-ionic thermoplastic polymers have a weight average molecular weights between about 10,000 and 500,000 daltons, more preferably between about 20,000 and 400,000 daltons, are most preferably between about 30,000 and 300,000 daltons. Suitable non-ionic thermoplastic polymers have a flow rate, when tested according to ASTM D1238-90b at the temperature used when extruding the blend, preferably between about 0.5 and 100 g/10 min., more preferably between about 1 and 50 g/10 min., most preferably between about 3 and 10 g/10 min.

The tubing and sheeting of the present invention is flexible, tough, abrasion resistant and heat formable. The tubing also possesses a remarkable resistance to kinking during bending and rekinking in a location that has already been kinked when compared to alternatives of similar cost. Embodiments which are chlorine-free are described. These embodiments do not release harmful chemicals such as hydrogen chloride to the atmosphere when they are burned or otherwise degraded. The polymeric blends, tubing, and tubing assemblies of the present invention are also safe and effective for use in medical applications, and preferably for that application contain no plasticizers or other leachable or exudable ingredients which could contaminate pharmaceutical fluids. In particular, at least the fluid contacting surfaces of the tubing contain no phthalate or citrate esters or other plasticizers or additives which are capable of leaching into pharmaceutical fluids. The polymeric blends, tubing, and tubing assemblies also preferably avoid absorption of solvents, drugs, pharmaceutical agents and other materials which come in contact with them. This characteristic is especially desirable when the polymeric blend is formed into a tube and/or tube assembly and is used in a medical product. In this application, the tubing and tubing assemblies display minimal or no absorption of drug, pharmaceutical carrier or other pharmaceutical liquid. Optionally, the tubing and tubing assemblies can be composed of thermoplastic polymers which will make the layers resistant to acid, solvent, UV light, and gamma sterilization, and will render the tube and tube assembly clear or opaque or colored.

The preferred method of preparing tubing according to the present invention is by extrusion. Most preferably, the components are thoroughly mixed prior to being charged to the extruder (e.g., pellets of the individual materials are blended together prior to being charged into the extruder where they are further mixed by the extruder and extruded). Alternatively, the materials may be individually metered into the extruder in the correct proportion. Once the tubing has been extruded in appropriate lengths and sizes, tubing assemblies may be formed by bonding these lengths to one or more plastic fluid transporting components. Noteworthy among these plastic fluid transporting components are non-PVC pumping cassettes formed from multi-layer films as discussed in copending and coassigned U.S. patent application Ser. No. 08/103,082. As discussed therein, a cassette may be bonded to non-PVC tubing by appropriate adhesives, or may advantageously be performed by applying a mixture of a polymeric binder and susceptor particles to the apparatus, placing parts of the apparatus, in contact with each other, and subjecting the combination to electromagnetic radiation. The susceptor particles absorb electromagnetic energy and generate heat. This heats the polymeric binder material and heat welds the components together. Additional information about the preferred susceptor bonding technique is described in coassigned U.S. patent applications Ser. No. 07/588,591, 07/668,974, and 07/800,632, the disclosures of which are incorporated herein by reference.

The tubing is preferably prepared with an outside diameter (O.D.) of between about 1 and 13 mm, more preferably between about 2 and 7 mm, and most preferably between about 2 and 5 min. Examples of suitable tubing include: tubing for use with medical syringe sets (e.g., having an O.D. of about 2 mm and an inside diameter (I.D.) of between about 0.7 and 0.8 mm); tubing for use with arthroscopy sets (e.g., having an O.D. of about 9.5 mm and an I.D. of 6.3 mm or an O.D. of about 8 mm and an I.D. of 4.8 mm); tubing used during cardiopulmonary surgery (e.g., having an O.D.

between about 4.8 to 12.7 mm and an I.D. between about 1.6 to 8 mm); microbore tubing for use with flow control devices, and blood diagnostic devices (e.g., having an O.D. about 1.5 mm and an I.D. between about 0.13 to 0.38 mm); and other surgical tubing. For medical tubing used with infusion pumps, the tubing is preferably prepared with an (O.D.) of between about 3 and 6 mm, more preferably between about 3 and 4.5 mm, and most preferably, medical tubing is provided having an O.D. of about 3.6 or 4.1 mm.

The relative dimensions of the walls of the tubing made from the described materials to its lumen have been found to have a surprisingly substantial impact on the kink and rekink resistance on the final tubing. For blend tubing according to the present invention having an O.D. of 4.06 mm, the I.D. of the tube is preferably less than 3.05 mm, more preferably less than 2.85, and most preferably less than 2.65 mm. For blend tubing according to the present invention having an O.D. of 3.6 mm, the I.D. of the tube is preferably less than 2.6 mm, more preferably less than 2.4, and most preferably less than 2.2 mm.

To provide specific additional characteristics to the tubing and tubing assemblies of the present invention the polymer blend can also contain conventional, preferably non-leachable, additives such as antistatic materials, pigments, dyes, ultraviolet absorbers, nucleating agents, quenching agents and the like. For example, ultraviolet absorbers can be added to one or more of the layers of the tubing and tubing assemblies for application in IV cassettes used with light-sensitive drugs.

Tubing and tubing assemblies according to the present invention can be utilized in a wide range of both medical and non-medical products. In the medical area the tubing and tubing assemblies are suitable for replacing chlorine-containing PVC tubing, such as is utilized with IV fluid administration sets, infusion sets, cassettes, arthroscopy fluid control systems, cardiovascular systems and blood gas monitoring systems.

Kink/rekink Resistance Test Method

The Kink/Rekink Resistance Test Method is used to determine the resistance of a tubing sample to a sudden buckling collapse which seals off or substantially restricts the flow of fluid through the lumen of the tubing sample when the sample is bent back towards itself over too small a radius. Once such a collapse (hereafter called a kink) has occurred in a polymeric tubing sample, there typically is a strained area which is thereafter particularly susceptible to a similar failure (hereafter called a rekink). Rekinking can occur at a larger tubing bend radius than is required to cause the original kink. In particular, during typical IV therapy it is conventional to loop the IV tubing 180 degrees and tape the loop to a patient's wrist. A possibility of a kink in the IV line in that loop or elsewhere is a recognized complication in delivering IV therapy and must be guarded against by medical practitioners. This method is used to compare the characteristics of a flexible tube with respect to its ability to resist kinking and rekinking. The test is suitable for tubing having I.D.'s between 1.27 and 6.35 mm. The test is conducted at room temperature (approximately 23° C.). A similar method has been previously discussed in copending and coassigned U.S. patent application Ser. No. 08/104,256 "Multilayer Tubing" to Wilfong et al.

Figure 3A:
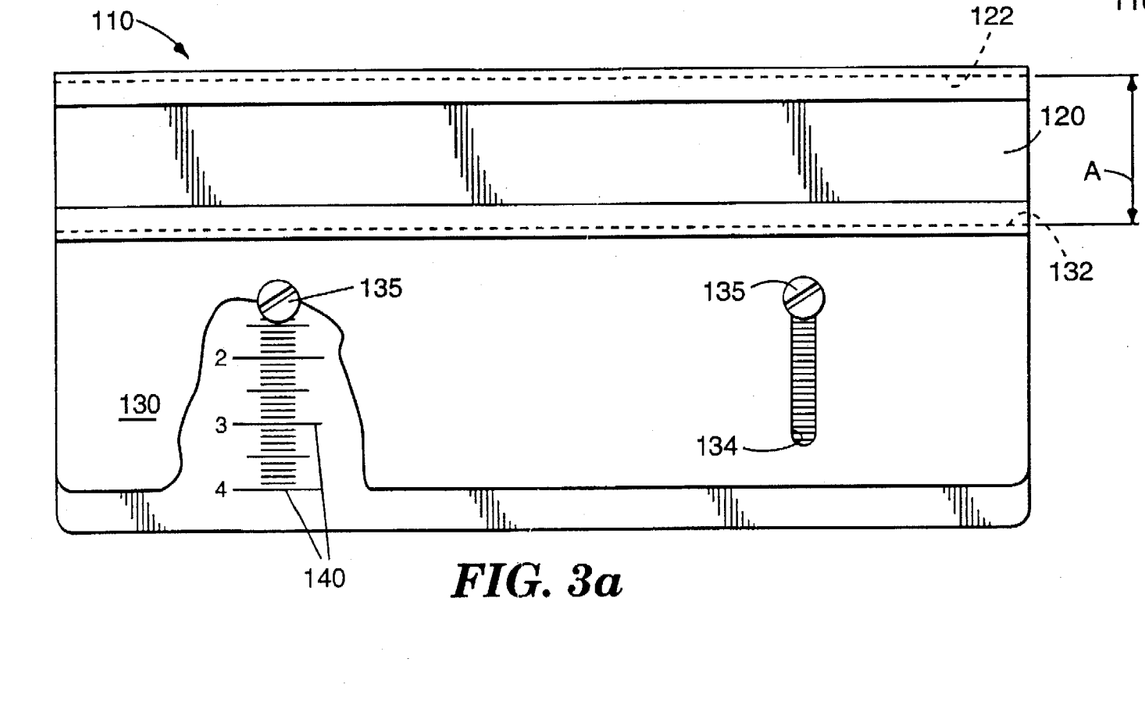
FIG. 3a is a front plan view of a "Kink-o-meter"
Figure 3B:
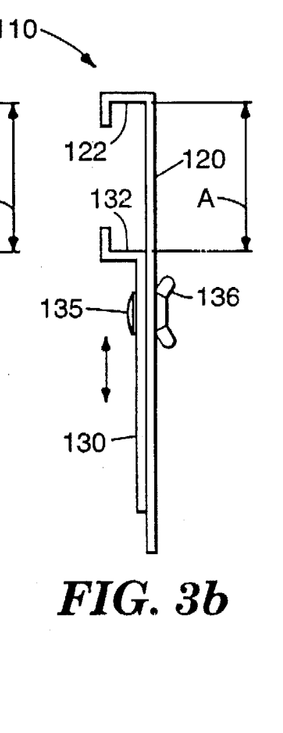

Referring now to FIGS. 3a and 3b, the test is conducted on a test apparatus 110 (Kink-O-Meter) used to measure kink and rekink resistance of a tubing sample. The test apparatus 110 includes a lower plate 120 having a lip 122 along one edge. Two threaded bolts 135 are mounted on the lower plate 120. An upper plate 130 having a lip 132 along one edge and two slots 134 is mounted in sliding engagement with lower plate 120 with the threaded studs 135 fitting into the two slots 134 in such a way that the lips 122 and 132 are aligned parallel to each other and separated by a distance "A". A pair of wing nuts 136 are mounted on the threaded bolts to provide a convenient amount of sliding resistance between the lower plate 120 and the upper plate 130. Marking numerals 140, which are read against the edge of the upper plate 130, are provided on lower plate 120 in order to quantify the results. The marking numerals 140 correspond to the distance the plates are separated in centimeters, i.e., the marking numerals correspond to distance "A" shown in FIGS. 3a and 3b.

The procedure for determining kink and rekink resistance with the Kink-O-Meter is as follows:

1. Cut a tubing sample at least 30 cm long.
2. Move the upper plate on the test apparatus until the space between the lip of the upper plate and the lip of the lower plate (shown as "A" in FIGS. 3a and 3b) is fully open (~4 cm).
3. Curl the tubing samples into a "U" shape and place it into the trough formed between lips 122 and 132.
4. Slowly slide the upper plate to decrease the width of the trough thus decreasing the radius of curvature of the tubing sample until the tubing sample kinks. The rate of sliding should be slow and uniform, at a rate which will take 10 to 15 seconds from the opened position to the closed position.
5. Reading the marking numerals, record the number exposed on the lower plate along the bottom edge of the upper plate which is identified as the "kink number".
6. Mark the tubing sample with ink at the kink location.
7. Remove the tubing sample from the trough and press the sides of the "U" shape tubing sample together to assure full tube kinking.
8. Straighten the tubing sample to open the kink.
9. After 30 seconds, place the tubing sample in the back in the trough so that the kink area is at the bottom of the "U".
10. Repeat step 4 until the tubing sample kinks again.
11. Record the number exposed on the lower plate along the bottom edge of the upper plate which is identified as the "rekink number".

The tubing of the present invention have been found to be surprisingly resistant to kink and rekink. When tested as described above, preferred medical tubing having an O.D. of about 4.06 mm and an I.D. of about 2.8 mm resists kink, when bent into a "U" shape between the edges of a trough, to a separation distance of less than 3.5 cm, more preferably less than 3.0 cm, and most preferably less than 2.8 cm. When tested as described above, preferred medical tubing having an O.D. of about 4.06 mm and an I.D. of about 2.8 mm resists rekink, when bent into a "U" shape between the edges of a trough, to a separation distance of less than 3.5 cm, more preferably less than 3.0 cm, and most preferably less than 2.8 cm.

EXAMPLES

Example 1

Five runs of extruded tubing were made from a polymer blend. The blend was made from 70 parts by weight of a non-ionic thermoplastic ethylene/butene copolymer, commercially available as Exact 4024; and 30 parts by weight of the blend of an ionomeric terpolymer of polyethylene, acrylate, and methacrylic acid, neutralized with zinc and commercially available as Surlyn 9320. The physical properties other than dimension were measured variously 1 to 2 months after extrusion. Extrusion was performed in a 2 inch extruder commercially available as Model 200 from Welex Co. of Blue Bell, Pa. Extrusion conditions were as detailed in Table 1a.

TABLE 1a

| Barrell diam. (cm) | 5 |
|---|---|
| Zone 1 (°C.) | 127 |
| Zone 2 (°C.) | 213 |
| Zone 3 (°C.) | 250 |
| Zone 4 (°C.) | not used |
| Melt Temp (°C.) | 260 |
| Die Temp (°C.) | 265 |
| RPM | 63 |
| Pressure (MPa) | 16.5 |
| Amps | 21 |
| Water Temp (°C.) | 25 |
| Puller Speed (m/min) | 122 |

The samples obtained had properties as detailed in Table 1b. The tensile and elongation measurements were made on each sample using a tensile testing apparatus commercially available as Model 2122 from Instron Corp. of Canton, Mass. The gauge length for the tests was initially set to 5.08 cm, with the rate of elongation set to 51 cm per minute. For each tubing sample three replicas were run, with the data averaged for the Table below. The Young's modulus in Table 1b is a computed value of the maximum slope of the stress/strain curve developed at 0% strain. The toughness is a computed value of the integral area of the stress/strain curve.

TABLE 1b

| Run number | OD (cm) | ID (cm) | Kink number (cm) | Rekink number (cm) | Young's Modulus (MPa) | Tensile strength (MPa) | Elongation (%) | Toughness (kg-%) |
|---|---|---|---|---|---|---|---|---|
| 1 | 0.41 | 0.28 | 2.54 | 2.79 | 21.43 | 18.27 | 840 | 5468 |
| 2 | 0.41 | 0.28 | 2.41 | 2.79 | 20.33 | 17.85 | 850 | 5332 |
| 3 | 0.37 | 0.26 | 2.41 | 2.79 | 23.40 | 17.69 | 782 | 5091 |
| 4 | 0.36 | 0.24 | 2.03 | 2.54 | 22.39 | 19.13 | 809 | 4955 |
| 5 | 0.35 | 0.24 | 2.03 | 2.54 | 22.31 | 18.81 | 826 | 4627 |

Example 2

Six more runs were made similarly to the runs of Example 1, except for the following particulars. The blend was made from 70 parts by weight of a non-ionic thermoplastic ethylene/butene copolymer, commercially available as Exact 4028; and 30 parts by weight of an ionomeric terpolymer of polyethylene, acrylate, and methacrylic acid, neutralized with zinc and commercially available as Surlyn 9320. The process conditions on the extruder are as shown in Table 2a. The dimensions selected and the physical properties of the resulting samples are displayed in Table 2b.

TABLE 2a

| Barrel diam. (cm) | 5 |
|---|---|
| Zone 1 (°C.) | 127 |
| Zone 2 (°C.) | 213 |
| Zone 3 (°C.) | 249 |
| Zone 4 (°C.) | not used |
| Melt Temp (°C.) | not recorded |
| Die Temp (°C.) | 265 |
| RPM | 42 |
| Pressure (MPa) | 8.3 |
| Amps | 14 |
| Water Temp (°C.) | 25 |
| Puller Speed (m/min) | 78 |

TABLE 2b

| Run number | OD (cm) | ID (cm) | Kink number (cm) | Rekink number (cm) | Young's Modulus (MPa) | Tensile strength (MPa) | Elongation (%) | Toughness (kg-%) |
|---|---|---|---|---|---|---|---|---|
| 1 | 0.41 | 0.28 | 2.41 | 3.05 | 17.66 | 14.77 | 922 | 4864 |
| 2 | 0.41 | 0.27 | 2.16 | 2.67 | 17.05 | 14.46 | 922 | 4950 |
| 3 | 0.36 | 0.24 | 2.03 | 2.29 | 18.47 | 13.93 | 872 | 4564 |
| 4 | 0.35 | 0.25 | 2.24 | 2.54 | 18.94 | 14.79 | 833 | 4677 |
| 5 | 0.36 | 0.25 | 2.29 | 2.67 | 21.25 | 14.46 | 791 | 4623 |
| 6 | 0.35 | 0.24 | 1.91 | 2.54 | 18.98 | 13.04 | 817 | — |

Example 3

Six more runs were made similarly to the runs of Example 1, except for the following particulars. The blend was made from 75 parts by weight of a non-ionic thermoplastic ethylene/butene copolymer, commercially available as Exact 4024; and 25 parts by weight of an ionomeric copolymer of polyethylene and methacrylic acid, neutralized with metal ion and commercially available as Surlyn 8255. The process conditions on the extruder are as shown in Table 3a. The dimensions selected and the physical properties of the resulting samples are displayed in Table 3b.

TABLE 3a

| Barrel diam. (cm) | 5 |
|---|---|
| Zone 1 (°C.) | 127 |
| Zone 2 (°C.) | 196 |
| Zone 3 (°C.) | 213 |
| Zone 4 (°C.) | not used |
| Melt Temp (°C.) | 260 |
| Die Temp (°C.) | 246 |
| RPM | 43 |
| Pressure (MPa) | 11 |
| Amps | 16 |
| Water Temp (°C.) | 25 |
| Puller Speed (m/min) | 152 |

TABLE 3b

| Run number | OD (cm) | ID (cm) | Kink number (cm) | Rekink number (cm) | Young's Modulus (MPa) | Tensile strength (MPa) | Elongation (%) | Toughness (kg-%) |
|---|---|---|---|---|---|---|---|---|
| 1 | 0.41 | 0.29 | 2.67 | 3.30 | 20.47 | 17.40 | 837 | 4809 |
| 2 | 0.40 | 0.27 | 2.29 | 2.67 | 22.48 | 18.11 | 898 | 4977 |
| 3 | 0.36 | 0.03 | 2.29 | 2.92 | 21.61 | 16.80 | 773 | 4487 |
| 4 | 0.35 | 0.25 | 2.54 | 3.18 | — | — | — | — |
| 5 | 0.36 | 0.24 | 2.03 | 2.79 | 23.01 | 15.74 | 823 | — |
| 6 | 0.36 | 0.24 | 2.16 | 2.79 | 21.53 | 14.94 | 830 | — |

Example 4

Five more runs were made similarly to the runs of Example 1, except for the following particulars. The blend was made from 70 parts by weight of a non-ionic thermoplastic ethylene/butene copolymer, commercially available as Exact 4024; and 30 parts by weight of an ethylene/acrylate/acrylic acid copolymer with zinc neutralization, commercially available as Iotek 7520. The process conditions on the extruder are as shown in Table 4a. The dimensions selected and the physical properties of the resulting samples are displayed in Table 4b.

TABLE 4a

| Barrel diam. (cm) | 5 |
|---|---|
| Zone 1 (°C.) | 127 |
| Zone 2 (°C.) | 213 |
| Zone 3 (°C.) | 249 |
| Zone 4 (°C.) | not used |
| Melt Temp (°C.) | 257 |
| Die Temp (°C.) | 266 |
| RPM | 36 |
| Pressure (MPa) | 11 |
| Amps | 15.5 |
| Water Temp (°C.) | 25 |
| Puller Speed (m/min) | 150 |

TABLE 4b

| Run number | OD (cm) | ID (cm) | Kink number (cm) | Rekink number (cm) | Young's Modulus (MPa) | Tensile strength (MPa) | Elongation (%) | Toughness (kg-%) |
|---|---|---|---|---|---|---|---|---|
| 1 | 0.41 | 0.28 | 2.54 | 3.18 | 20.84 | 15.30 | 805 | 4158 |
| 2 | 0.40 | 0.26 | 2.16 | 2.54 | 20.42 | 17.10 | 835 | 4539 |
| 3 | 0.37 | 0.26 | 2.29 | 3.05 | 19.97 | 16.60 | 781 | 4390 |
| 4 | 0.36 | 0.26 | 2.54 | 3.30 | 22.65 | 15.72 | 703 | 3825 |
| 5 | 0.36 | 0.25 | 2.03 | 2.54 | 22.36 | 16.28 | 711 | — |

Example 5

One more run was made similarly to the runs of Example 1, except for the following particulars. The blend was made from 70 parts by weight of a non-ionic thermoplastic ethylene/butene copolymer, commercially available as Exact 4041; and 30 parts by weight of an ionomeric copolymer of polyethylene, acrylate, and methacrylic acid, neutralized with metal ion and commercially available as Surlyn 8320. The process conditions on the extruder are as shown in Table 5a. The dimensions selected and the physical properties of the resulting samples are displayed in Table 5b.

TABLE 5a

| Barrel diam. (cm) | 5 |
|---|---|
| Zone 1 (°C.) | 121 |
| Zone 2 (°C.) | 177 |
| Zone 3 (°C.) | 218 |
| Zone 4 (°C.) | not used |
| Melt Temp (°C.) | — |
| Die Temp (°C.) | 218 |
| RPM | 47 |
| Pressure (MPa) | — |
| Amps | 16 |
| Water Temp (°C.) | 25 |
| Puller Speed (m/min) | 61 |

TABLE 5b

| Run number | OD (cm) | ID (cm) | Kink number (cm) | Rekink number (cm) | Young's Modulus (MPa) | Tensile strength (MPa) | Elongation (%) | Toughness (kg-%) |
|---|---|---|---|---|---|---|---|---|
| 1 | 0.41 | 0.28 | 2.16 | 2.92 | 22.2 | 14.6 | 843 | — |

Example 6

Comparative Examples

Certain of the materials of the examples above were extruded in an unblended form on the same extruder in order to provide comparison. The physical properties measured from the runs are summarized in Table 6a.

TABLE 6a

| Material | OD (cm) | ID (cm) | Kink number (cm) | Rekink number (cm) | Young's Modulus (MPa) | Tensile strength (MPa) | Elongation (%) |
|---|---|---|---|---|---|---|---|
| Exact 4024 | 0.4 | 0.27 | 2.67 | 3.56 | 14.7 | 19.5 | 1039 |
| Exact 4028 | 0.4 | 0.27 | 2.54 | 3.30 | — | — | — |
| Surlyn 8255 | 0.4 | 0.27 | 2.41 | 3.56 | 46.0 | 31.0 | 450 |
| Surlyn 8320 | 0.4 | 0.27 | 2.29 | 3.05 | 25.5 | 15.5 | 435 |
| Surlyn 9320 | 0.4 | 0.27 | 2.41 | 2.92 | 23.4 | 19.4 | 700 |

Each of the tube samples produced in these comparative runs had some property which made it less suitable than the blend materials. The tube made from the Exact resins had a poor rekink property, had a tacky surface that picks up dirt easily, had a strong cold set memory, and did not bond well with adhesives of the sort used to fabricate tubing assemblies. The tube made from the Suflyn 8255 material was stiff in the hands, and also had a poor rekink property. Although the tubes made from the Surlyn 8320 and 9320 resins have acceptable mechanical and kink properties, the Surlyn resins are poor in heat stability and are too expensive to use in pure form for disposable medical assemblies.

The low softening temperature of the Surlyn resins make them undesirable for use as medical tubing. The heat stability of certain materials was measured using a thermal mechanical analyzer equipped with a 50 mN penetration probe and operated over a temperature sweep from 0° C. to 100° C. at a rate of 10° C. per minute. The Surlyn 8320 resin has a softening point (i.e., the temperature at which the material begins to soften and the 50 mN probe begins to penetrate the sample) of about 42° C. In contrast, a blend of 25 parts Surlyn 8320 with 75 parts Exact 4024 resin exhibits a softening point of about 65° C.

Various modifications and alterations of the present invention will be apparent to those skilled in the art without departing from the scope and spirit of this invention, and it should be understood that this invention is not limited to the illustrative embodiments set forth herein.

What is claimed is:

1. A tube, comprising:
   a polymeric material having at least one lumen therein, the polymeric material comprising a blend of a thermoplastic ionomer and a non-ionic thermoplastic polymer, wherein the thermoplastic ionomer is present in an amount between about 10 and 50% by weight and has a Young's modulus less than about 56 MPa, and the non-ionic thermoplastic polymer is present in an amount between about 50 and 90% by weight, and wherein the tube has a Young's modulus between about 14 to 35 MPa.

2. A tube according to claim 1, wherein the tube has a Young's modulus between about 17 and 28 MPa.

3. A tube according to claim 1, wherein the thermoplastic ionomer is present in an amount between about 20 and 40% by weight, and the non-ionic thermoplastic polymer is present in an amount between about 60 and 80% by weight.

4. A tube according to claim 1, wherein the tube has an outside diameter between about 3 mm and 4.5 mm.

5. A tube according to claim 1, wherein the thermoplastic ionomer comprises an organic backbone and has pendant acidic groups selected from the group consisting of carboxylic acid groups and sulfonic acid groups.

6. A tube according to claim 1, wherein the non-ionic thermoplastic polymer is selected from the group consisting of polymers of olefin monomers and copolymers of olefin monomers and substituted olefin monomers.

7. A tube according to claim 1, wherein the non-ionic thermoplastic polymer is selected from the group consisting of polymers of a C2 to C4 mono-unsaturated alkene; copolymers of a majority of a C2 to C4 mono-unsaturated alkene with a minority of a substituted C4 to C14 mono-unsaturated alkene; and copolymers of a majority of a C2 to C4 mono-unsaturated alkene with a minority of a substituted C2 to C6 mono-unsaturated alkene having a substituent carboxylic acid ester group.

8. A tube according to claim 1, which contains essentially no medically harmful substance capable of leaching into an aqueous based or organic based fluid in contact with the inside surface of the film.

9. A tube according to claim 1, which is essentially free of chlorine.

10. A tube according to claim 1, wherein said polymeric material, when formed into a tube having an outside diameter of 4.06 mm and an inside diameter of 2.8 mm, resists kink when bent into a "U" shape between the edges of a trough having a separation distance of 3.0 cm.

11. A tube according to claim 1, wherein said polymeric material, when formed into a tube having an outside diameter of 4.06 mm and an inside diameter of 2.8 mm, resists rekink when bent into a "U" shape between the edges of a trough having a separation distance of 3.3 cm.

12. A tube according to claim 1, wherein said polymeric material has an elongation of at least 600%.

13. A tube according to claim 1, wherein said polymeric material has a tensile strength of at least 14 MPa.

14. A tube, comprising:
   a length of a single layer of polymeric material having at least one lumen therein, the polymeric material comprising a blend of:
   a thermoplastic ionomer having a tensile modulus between about 14 and 56 MPa; the ionomer present in an amount between about 10 and 50% by weight; and
   a non-ionic thermoplastic polymer having a Young's modulus between about 14 and 35 MPa; the non-ionic thermoplastic polymer present in an amount between about 50 and 90% by weight.

15. A tube, comprising:

a polymeric material having at least one lumen therein, the polymeric material comprising a blend of:

a thermoplastic ionomer selected from the group consisting of copolymers of ethylene and acrylic acid-metal cation neutralized salt, and ethylene and methacrylic acid-metal cation neutralized salt, and present in an amount between about 10 and 50% by weight and having a Young's modulus less than about 56 MPa; and a non-ionic thermoplastic polymer selected from the group consisting of polymers of olefin monomers and copolymers of olefin monomers and substituted olefin monomers, and present in an amount between about 50 and 90% by weight, wherein the tube has a Young's modulus between about 14 to 35 MPa.

16. A tube according to claim 15, wherein the thermoplastic ionomer is present in an amount between about 20 and 40% by weight; the non-ionic thermoplastic polymer is present in an amount between about 60 and 80% by weight; and the tube has an outside diameter of between about 3.5 and 3.7 mm and an inside diameter less than 2.6 mm.

17. A tube according to claim 15, wherein the thermoplastic ionomer is present in an amount between about 20 and 40% by weight; the non-ionic thermoplastic polymer is present in an amount between about 60 and 80% by weight; and the tube has an outside diameter of between about 3.9 and 4.1 mm and an inside diameter less than 3.1 mm.

* * * * *